United States Patent
Erskine et al.

(12)

(10) Patent No.: US 6,516,633 B1
(45) Date of Patent: Feb. 11, 2003

(54) PHOTOCHROMIC GLASS NANOPARTICLES AND METHODS OF PREPARATION

(75) Inventors: Lael L. Erskine, Fremont, CA (US); Dan B. Millward, Alameda, CA (US); David S. Soane, Piedmont, CA (US)

(73) Assignee: Nano-Tex, LLC, Emeryville, CA (US)

( * ) Notice: Subject to any disclaimer, the term of this patent is extended or adjusted under 35 U.S.C. 154(b) by 19 days.

(21) Appl. No.: 09/935,065

(22) Filed: Aug. 22, 2001

Related U.S. Application Data

(60) Provisional application No. 60/228,513, filed on Aug. 28, 2000.

(51) Int. Cl.$^7$ ............... C03B 19/10; C03B 19/12
(52) U.S. Cl. ............... 65/21.1; 65/21.4; 65/17.2; 65/30.11; 423/38; 423/42; 423/46
(58) Field of Search ............... 65/30.11, 17.2, 65/21.1, 21.4; 423/38, 46, 42

(56) References Cited

U.S. PATENT DOCUMENTS

| | | |
|---|---|---|
| 5,837,025 A | 11/1998 | Auchter-Krummel et al. ............... 65/21.1 |
| 5,879,715 A | 3/1999 | Higgins et al. ............... 424/489 |

OTHER PUBLICATIONS

Pillai et al., *Adv. In Coll. and Interface Sci.*, 55: 241–269 (1995) (Elsevier Science B.V.).

*Primary Examiner*—Michael Colaianni
(74) *Attorney, Agent, or Firm*—Jacqueline S. Larson

(57) ABSTRACT

The present invention is directed to microemulsion techniques for rapidly preparing photochromic glass nanoparticles and to the photochromic glass nanoparticles so prepared. More particularly, the method of the invention comprises the combination of two microemulsions, one containing a water-soluble silver salt and a glass precursor and the other containing a halide salt and an initiator for glass formation, which process rapidly yields silver halide particles. This invention gives nanometer-sized silver halide particles embedded in glass, thus providing photochromic glass nanoparticles without further annealing, or at most mild annealing. These nanoparticles are valuable as added components to any macro-material that one might wish to have photochromic properties. The particles would impart photochromism while not affecting the physical properties of the material.

6 Claims, No Drawings

PHOTOCHROMIC GLASS NANOPARTICLES AND METHODS OF PREPARATION

This application claims benefit of Provisional patent application Ser. No. 60/228,513 filed on Aug. 28, 2000; the entire disclosure of which is incorporated herein by reference.

FIELD OF INVENTION

This invention is directed to a process for production of colloidal photochromic glass nanoparticles, that is, unagglomerated particles of ca. 100 nm or less in diameter.

BACKGROUND OF INVENTION

Nanotechnology, defined broadly as the manufacturing and application of nanometer-sized materials (e.g. nanoparticles), is experiencing unprecedented research and development, largely due to the unique and valuable properties of such materials. In particular, the application of nanoparticles to macro-sized materials can add novel properties to the macro-sized material, without alteration of desired physical properties inherent to the macro-material. These synergies do not exist when two macro-materials are combined.

One method for the controlled syntheses of numerous types of nanoparticles is "microemulsion-mediated" synthesis. This technique consists of combining differing amounts of two immiscible liquids and a surfactant or surfactant mixture. A surfactant is an ambiphilic molecule containing at least two segments, each of which is soluble in one of the two immiscible liquid phases. Surfactants act by decreasing the surface tension between the two phases, resulting in a dispersion of droplets called "micelles", between 2 and 50 nm in size, with the lesser volume of liquid (the disperse phase) within the other liquid (the continuous phase). Most commonly, the continuous phase is water and the dispersed phase is a hydrocarbon oil. A dispersion of water in oil is called a reverse micelle dispersion.

The reverse micelles function as "nano-reactors" for reactions of molecules that dissolve exclusively in the aqueous phase. Brownian motion causes the micelles to continuously collide, coalesce, and break apart, resulting in constant exchange of the contents of the micelles. The addition of a reverse micelle dispersion or aqueous solution of reactant A to a reverse micelle dispersion of reactant B will cause reaction between A and B to afford product C as micelles containing the reactants collide and coalesce.

While highly controllable, the size of the nanoparticles produced is not directly related to micelle size and is not easily correlated to the concentration of reactants. An important factor governing particle size is the ratio R of the rate of nucleation ($r_n$) to the rate of growth or agglomeration ($r_g$), where $R=r_n/r_g$. A large ratio provides many, very small particles, whereas a smaller ratio results in fewer, larger particles. These competing factors can be empirically controlled by variation of reactant concentration and microemulsion compositional parameters (stirring speed, surfactant choice, amount of surfactant used, and temperature). Shah has reviewed the state of the art in this area. (Pillai et al., *Adv. In Coll. and Interface Sci.*, 55,241 (1995)).

These techniques have been employed to produce monodisperse inorganic nanoparticles, which can be purified on an industrial scale through cross-flow membrane filtration (U.S. Pat. No. 5,879,715). Mono-disperse glass nanoparticles have also been produced by addition of basic aqueous solutions to a reverse micelle emulsion containing silica sol and other inorganic glass components (U.S. Pat. No. 5,837,025). The basic solution causes precipitation of glass nanoparticles within the micelles. The resulting nanoparticles are isolated by temperature-induced phase separation, washing, and centrifugation.

Photochromic glass absorbs visible light (darkens) upon exposure to actinic radiation, e.g. ultraviolet light, and ceases absorption (fades) when the actinic radiation is removed. This reversible behavior is ascribed to nanocrystalline silver halide particles dispersed in the glass. Reversible ionization of the silver halide causes the photochromic effect. It is noteworthy that the silver halide particles must be isolated for reversibility; this is the function of the glass. In many embodiments, small amounts of copper(I) salts are also embedded in the glass; the copper sensitizes the silver halide particles to UV light.

In typical production, the silver halide is included in the glass melt and the melt is shaped into the desired form and cooled. Often, the shaped product is not photochromic and must be heated to a temperature between the annealing point and the softening point of the glass, typically between 500° and 900° C. This heating allows for a phase separation of the silver halide within the glass. The resulting nanocrystals need to be 5 nm or greater in size to exhibit photochromic behavior. It would be desirable to develop a process of forming nanoparticles of silver halide and embedding them in glass. Such a process would avoid the extra costs associated with the annealing process.

At present there are no methods described in the literature for preparing photochromic glass nanoparticles.

SUMMARY OF THE INVENTION

The present invention is directed to microemulsion techniques for rapidly preparing photochromic glass nanoparticles and to the photochromic glass nanoparticles so prepared.

More particularly, the method of the invention comprises the combination of two microemulsions, one microemulsion containing a water-soluble silver salt and glass precursors and the other microemulsion containing a halide salt and an initiator for glass formation, which process rapidly yields glass-encased silver halide particles. This invention gives nanometer-sized (preferably about 100 nm or less in diameter) unagglomerated silver halide particles embedded in glass, thus providing photochromic glass nanoparticles without further annealing, or at most mild annealing. Preparation of these nanoparticles can be at ambient or slightly elevated temperature. These nanoparticles would be valuable as added components to any macro-material that one might wish to have photochromic properties. The particles would impart photochromism while not affecting the physical properties of the material. In one embodiment of the invention, the photochromic glass nanoparticles comprise reactive sites on their surface to allow attachment of the nanoparticles to macro-materials.

This invention is further directed to fibers, yarns, fabrics (which may be woven, knitted, stitch-bonded or nonwoven), other textiles, or finished goods (encompassed collectively herein under the terms "textiles" or "webs") treated with the photochromic glass nanoparticles. Such textiles and webs exhibit the property of reversible, light-induced darkening.

DETAILED DESCRIPTION OF THE INVENTION

The method of the present invention comprises two parallel but non-interactive reactions, namely the formation of silver halide and the formation of glass. The reactions occur coincidentally in the same reverse micelle reactors. The reactions are initiated by combining two distinct precursor microemulsions. Each precursor microemulsion is chemically stable, as it contains only one or some of the components for each reaction. The components for formation of a silver halide nanoparticle are a water-soluble silver salt and a halide salt. The components for formation of glass are a glass composition comprising glass precursors and an initiator of glass formation. It is apparent that the precursor microemulsions must be constructed such that the reactive components are kept apart until mixing, but no other restriction on the microemulsion composition is implied. Thus, one preferred embodiment consists of a first precursor microemulsion containing a soluble silver salt and the glass-forming components, and a second precursor microemulsion containing a halide salt and an initiator of glass formation.

The precursor microemulsions are prepared by methods known in the art (see, for example, U.S. Pat. No. 5,837,025). The particulars of the preparation can be determined by one of skill in the art without undue experimentation.

Those skilled in the art will recognize that the rates of the two reactions are different. Insoluble silver halide particles form almost instantaneously when silver salts and halide salts are combined, whereas glass synthesis occurs at a slower rate. In the present invention, as the reactions occur in the combined reverse micelles, the resulting silver halide nanoparticles will remain dispersed within the micelles. Glass formation will then encase the suspended silver halide nanoparticles within a glass matrix. In a preferred embodiment, one precursor microemulsion contains silver nitrate and the other contains sodium chloride.

The glass precursor composition comprises glass-forming components. The composition generally comprises a source of silica, such as a silica sol (a colloidal dispersion of glass). Glass sols are commercially available in a variety of compositions. In addition, the glass composition may include, but is not limited to, silicon dioxide ($SiO_2$), aluminum oxide ($Al_2O_3$), calcium oxide (CaO), disodium oxide ($Na_2O$), zinc oxide (ZnO), diborate ($B_2O_3$), or mixtures thereof. These may be present in the precursor composition as salts, examples of which are: aluminum nitrate-nonhydrate, calcium nitrate-tetrahydrate, sodium acetate, boric acid, and zinc nitrate-hexahydrate.

The initiator for glass formation can be any material that precipitates or solidifies the glass precursor composition. Glass particles can be generated in the microdroplets of the emulsion via precipitation reactions that can occur by varying or changing the pH value. In one embodiment, the addition of base to a silica glass sol initiates the aggregation of the colloids into larger particles. The base may consist of any base capable of inducing sol aggregation. Presently preferred bases are alkali hydroxides and alkali earth hydroxides. Sodium hydroxide is particularly preferred.

Alternatively, dissolved glass in dispersed, alkaline aqueous droplets may be solidified/precipitated by acidification of the reverse microemulsion. In this embodiment, any acid capable of initiating solidification may be employed as the initiator for glass formation. Halide acids are particularly preferred in this embodiment as they can induce both silver halide nanoparticle formation and glass formation.

In one embodiment of the invention, capping agents are added to the combined microemulsion upon formation of the glass nanoparticles. These agents will perform up to three functions: they will form a coating around the glass, which will prevent agglomeration of the nanoparticles; they will provide reactive sites to allow attachment of the nanoparticles to macro-materials; and they may induce preferential dispersion of the nanoparticles into an aqueous phase. Preferred embodiments of the capping agents are combinations of alkylalkoxysilanes, epoxide-substituted alkoxysilanes, and quaternary ammonium-substituted alkoxysilanes, but any molecules that would react with the hydroxyl-terminated surface of the glass are considered to be capping agents within the scope of this invention. The capping agents, as well as any other species that mediates the capping reaction, may be added as a solution or a microemulsion.

The reactive sites or functional groups of the capping agents may be selected from those groups that will bind chemically with a particular structural element, macro-material, fiber, yarn, fabric, or finished good. For example, all cellulosic-based webs contain hydroxyl groups. Wool and other proteinaceous animal fibers, silk, and regenerated proteins contain hydroxyl, amine, carboxylate, and thiol groups (the latter as disulfides). It is desirable for the reactive sites to contain functional groups that are reactive to the fiber. For example, the capping agents may contain adjacent carboxyl groups that can form five- and six-membered cyclic anhydrides. The anhydrides form with the aid of a catalyst when the capping agent is heated and dried. These cyclic anhydrides react with fibers that contain hydroxyls or amines (e.g. cotton or wool). Alternatively, the reactive groups may contain epoxide groups or epoxide precursors, such as halohydrins. Epoxides can react with amines and hydroxyls. The capping agent may also comprise an N-methylolamide group, which reacts with hydroxyl groups at high temperatures and acidic pH. Anhydride groups are presently preferred.

Specific amine-reactive groups include isothiocyanates, isocyanates, acyl azides, N-hydroxysuccinimide esters, sulfonyl chlorides, aldehydes, glyoxals, epoxides, oxiranes, carbonates, arylating agents, imidoesters, carbodiimides, anhydrides, and halohydrins. Carboxylate-reactive groups include diazoalkanes and diazoacetyl compounds, carbonyl diimidazole, and carbodiimides. Hydroxyl-reactive functional groups include epoxides, oxiranes, carbonyl diimidazole, N,N'-disuccinimidyl carbonate or N-hydroxysuccinimidyl chloroformate, alkyl halides, isocyanates, and halohydrins. Hydroxyl groups may also be oxidized enzymatically or with periodate. Thiol groups react with haloacetyl and alkyl halide derivatives, maleimides, aziridines, acryloyl derivatives, arylating agents, and thiol-disulfide exchange reagents such as pyridyl disulfides, disulfide reductants, and 5-thio-2-nitrobenzoic acid.

Surface coverage of the capping agents may in a later step be further enhanced by contacting these particles with linker molecules, such as a polymer or polymer precursor for example, containing functional groups that react with the particles. These polymers or polymer precursors can assist as anchors to attach the nanoparticles to macroscopic materials through entanglement or chemical reaction. Each linker molecule may have more than one type of functional group, but at least one of the types of functionality will belong to a group that is reactive with the macro-material to be treated. The linkers may be grafted onto the glass nanoparticles prior to treatment of the macro-material, or they may be an additional component applied to the macro-material along with the glass nanoparticles. In the latter case, the linkers will bind to both the nanoparticles and the macro-material during the curing process. In one embodiment of the invention, the photochromic glass nanoparticles are attached via the functional groups of the capping agents to N-methylol resin compounds. These N-methylol compounds are then covalently attached to a textile or web, for example. The N-methylol-containing compounds thus act as attachment bridges or linkers between the glass nanoparticles and the textile. In the practice of the invention, the N-methylol compound may react first with either the fabric or the glass nanoparticle. An additional advantage is that the N-methylol-containing compound, when present in an appropriate amount will provide a durable press finish to the final nanoparticle-treated textile or web. Alternatively, there may be two or more linker molecules that are employed to link the photochromic glass nanoparticle to the textile.

After formation of the glass nanoparticles containing encased silver halide kernels, the combined emulsion must be separated to recover the nanoparticles. Prior to this final recovery step, the microemulsion may be heated to promote completion of reactions and annealing of all glass. The small size of the nanoparticles and the isolated nature of the dispersed phase ensure expedient annealing.

A significant problem with the use of microemulsion production techniques in the past has been the separation of nanoparticles from the microemulsion on any scale larger than bench-top synthesis. The most common technique is centrifugation, which is not suited for large-scale production. Cross-flow membrane filtration with an ultra-fine ceramic membrane is better suited for large-scale production, but the filters are very expensive and may become clogged. In this invention, the capping procedure is designed so that the coated particles will preferentially disperse in one of the phases. For example, capping with quaternary ammonium-substituted alkoxysilanes will produce a charged surface with a bias towards dispersion in an aqueous phase. Alternatively, capping with alkylalkoxysilanes will produce low surface energy particles which will preferentially disperse in an oil phase. After capping, an extraction with the preferred dispersal phase is employed to generate a phase separation, effectively overwhelming the surfactant. The phases are separated and the colloidal phase may be used directly or concentrated to isolate the nanoparticles. Alternatively, the mixture may be sprayed into a heated column. While the liquid dispersants evaporate, the particles fall to the bottom of the column and are collected in an aqueous bath.

The capped particles may be chemically attached to macroscopic materials by reaction of either the capping agent or a polymer bonded to the capping agent with reactive groups on the macroscopic surface. Alternatively, an uncapped particle may be exposed to a reactive, polycationic polymer, which would electrostatically coordinate to the negatively charged silica surface; the reactive portion of the polycationic polymer could then be used for chemical attachment to macroscopic materials. The nanoparticles may also optionally be dispersed in a coating material which is then applied to a macroscopic material. The coating adheres to the macroscopic material and holds the nanoparticles in place through entanglement.

The photochromic nanoparticles and material treated therewith have the property of light-induced, reversible darkening. That is, when exposed to light, the particles and treated material will darken. Upon removal of the light source, the particles and material will revert to their original shade. This invention is therefore useful in any application where reversible darkening is a desired property. In the textile industry, such darkening may be of interest as a fashion item or as a useful feature of items such as sheer drapery.

This invention is further directed to fibers, yarns, fabrics, textiles, or finished goods (encompassed herein under the terms "textiles" and "webs") treated with the photochromic glass nanoparticles. Such textiles or webs exhibit the property of reversible, light-induced darkening.

The novel webs of the present invention include fibers and/or filaments; woven, knitted, stitchbonded, and non-woven fabrics derived from natural, man made, and/or synthetic fibers and blends of such fibers; cellulose-based papers; and the like. They can comprise fibers in the form of continuous or discontinuous monofilaments, multifilaments, fibrids, fibrillated tapes or films, staple fibers, and yarns containing such filaments and/or fibers, and the like, which fibers can be of any desired composition. The fibers can be of natural, man made, or synthetic origin. Mixtures of natural fibers, man-made-fibers, and synthetic fibers can also be used. Included with the fibers can be non-fibrous elements, such as particulate fillers, flock, binders, sizes and the like. The textiles and webs of the invention are intended to include fabrics and textiles, and may be a sheet-like structure [woven (including jacquard woven for home furnishings fabrics) or non-woven, knitted (including weft inserted warp knits), tufted, or stitch bonded] and may be comprised of any of a variety of fibers or structural elements. The nonwovens may be stitch bonded, ultrasonic bonded, wet laid, dry laid, solvent extruded, air or gas blown, jet interlaced, hydroentangled, and the like, and may have a broad variety of properties including stretch, air permeability, or water vapor breathability. Examples of natural fibers include cotton, wool, silk, jute, linen, and the like. Examples of manmade fibers derived primarily from natural sources include regenerated cellulose rayon, Tencel® and Lyocell, cellulose esters such as cellulose acetate, cellulose triacetate, and regenerated proteins. Examples of synthetic fibers or structural elements include polyesters (including polyethyleneglycol terephthalate), wholly synthetic polyesters, polyesters derived from natural or biologic materials such as corn, polyamides (including nylon, such as nylon 6 and 6,6), acrylics, olefins such as polyethylene or polypropylene, aramids, azlons, modacrylics, novoloids, nytrils, aramids, spandex, vinyl polymers and copolymers, vinal, vinyon, and the like, and hybrids of such fibers and polymers.

To prepare webs having permanently attached photochromic glass nanoparticles, the fiber, the yarn, the fabric, or the finished good is exposed to a solution or dispersion/emulsion of the surface-capped photochromic glass nanoparticles (in one embodiment, preferably further surface-reacted with a polymer), by methods known in the art such as by soaking, spraying, dipping, fluid-flow, padding, and the like. If needed for the reaction, a catalyst is also present in the medium. The textile-reactive functional groups on the nanoparticle surface (either the surface capping agent or reacted polymer) react with the textile or web, by covalent bonding, to permanently attach to the textile. This curing can take place either before or after the treated textile is removed from the solution and dried, although it is generally preferred that the cure occur after the drying step.

In one embodiment, surface-capped photochromic glass nanoparticles reacted with a polymer containing excess hydroxyl groups are suspended in an aqueous solution that contains a compound having two or more N-methylol groups, such as DMDHEU or DMUG, and a Lewis acid catalyst, such as $MgCl_2$. A surfactant may be used to help suspend the particles. The fiber, the yarn, the fabric, the nonwoven web, or the finished good to be treated is then exposed to the solution containing the nanoparticles and the N-methylol-containing compounds, by methods known in the art such as by soaking, spraying, dipping, fluid-flow, padding, and the like. The N-methylol groups react with the web, by covalent bonding, and the functional groups on the surface of the nanoparticles react with the N-methylol-containing compounds to permanently attach the particles to the web. The treated web is then removed from the solution and dried.

The concentration of the photochromic glass nanoparticles in solution can be from about 0.05% to about 95%, preferably from about 0.1% to about 75%, more preferably from about 0.75% to about 50%, or from about 0.1% to about 5%; depending, however, on the rheological characteristics of the particular polymer nanoparticle selected (such as size or material) and on the amount of silver halide-loading or photochromic activity desired.

In preparing the treated textiles and webs of the invention, the process temperature can vary widely, depending on the affinity of the textile-reactive functional groups for the substrate. However, the temperature should not be so high as to decompose the reactants or damage the web, or so low as to cause inhibition of the reaction or freezing of the solvent. Unless specified to the contrary, the processes described herein take place at atmospheric pressure over a temperature range from about 5° C. to about 180° C., more preferably from about 10° C. to about 100° C., and most preferably at "room" or "ambient" temperature ("RT"), e.g. about 20° C. The time required for the processes herein will depend to a large extent on the temperature being used and the relative reactivities of the starting materials. Therefore, the time of exposure of the web to the polymer in solution can vary greatly, for example from about one second to about two days. Normally, the exposure time will be from about 1 to 30 seconds. Following exposure, the treated web is dried at ambient temperature or at a temperature above ambient, up to about 200° C. The pH of the solution will be dependent on the web being treated. For example, the pH should be kept at neutral to basic when treating cotton, because cotton will degrade in acid. Additionally, the deposition of nanoparticles with charged groups (e.g., amines, carboxylates, and the like) is expected to be dependent on solution pH. Salts (such as, for example, NaCl) may optionally be added to increase the rate of adsorption of anionic and cationic photochromic glass nanoparticles onto the web fibers. Unless otherwise specified, the process times and conditions are intended to be approximate.

The following examples are intended for illustrative purposes only and are in no way intended to be limiting.

EXAMPLES

Example 1

Irreversible photochromic silver halide nanoparticles were made by mixing two microemulsions. Microemulsion A was prepared by mixing together 60 g of hexanes, 16.75 g of polyoxyethylene(10) isooctylphenyl ether (trade name Triton X-100, Aldrich Chemical Co.), 13.25 g of n-hexanol, and 10 g of 0.1M silver nitrate (aq.). 60 Grams of hexanes, 16.75 g of Triton X-100, 13.25 g of n-hexanol, and 10 g of 0.1M sodium chloride (aq.) were stirred together to make microemulsion B. Each of these emulsions was stirred very quickly until it appeared clear to ensure the nanometer scale of the micelles. Then microemulsion B was quickly poured into microemulsion A, while minimizing the disruption of stirring in both emulsions. Instantaneously upon the addition of B to A, a white precipitate formed that was isolated by centrifugation. This yielded 0.8 g of a white precipitate that turned to a dark purple-gray upon exposure to ambient light overnight. As there was no silica in this synthesis, the nanoparticles obtained are not expected to be reversibly photochromic as they are not encased in glass.

Example 2

Reversible photochromic silver halide nanoparticles can be made by a method similar to that used in Example 1. Levasil 200S/30 (an acidic colloidal silica dispersion made by Bayer) is added to the 0.1 M silver nitrate used in microemulsion A, as glass precursor that will precipitate when the pH is raised. An addition of sodium hydroxide to the 0.1M sodium chloride in microemulsion B provides the base that is necessary to precipitate the colloidal silica when the two emulsions are mixed. Since the silver chloride precipitation is fast compared to the precipitation of the silica, the silver halide particle will be isolated by the silica causing reversible photochromic behavior from the resulting nanoparticles.

Example 3

A variation on Example 2 is one where only one microemulsion is made. Microemulsion A is prepared as it was in Example 2, possibly with some extra surfactant. Then while A is being stirred very quickly, 0.1M sodium chloride is added dropwise or in small portions, precipitating out the silver chloride. This is then followed by the dropwise addition of sodium hydroxide to precipitate the silica. This method has the advantage of stepwise precipitation to ensure that the silver halide particles are isolated by the silica. However, it has the disadvantage that it is more difficult to keep the reaction mixture a for microemulsion as non-emulsified reagents are added.

Example 4

Reversible photochromic nanoparticles can be made by adding dissolved silica at high pH to microemulsion A instead of the Levasil 200S/30, following the procedures of Example 2. Then microemulsion B will be made with hexanes, Triton X-100, n-hexanol, and HCl instead of NaCl or NaCl and base. The hydrochloric acid here provides a chlorine source to precipitate the silver halide and also lowers the pH and precipitates the silica. These reagents would also be amenable to the variant method described in Example 3.

Example 5

For photochromic nanoparticles with increased sensitivity to UV radiation, copper nitrate is added to any of the microemulsion A's described in Examples 2–4. The copper nitrate is added in amounts from 0.1 to 5 wt % of the silver nitrate used in microemulsion A to the aqueous phase of that microemulsion. When the precipitants are added, copper chloride will co-precipitate with silver chloride. The silver halide particles will be contaminated with copper, a sensitizer for photochromic behavior.

What is claimed is:

1. A method of preparing a photochromic glass nanoparticle, the method comprising:
    obtaining a first precursor reverse microemulsion having micelles comprising a water-soluble silver salt and glass-forming components;
    obtaining a second precursor reverse microemulsion having micelles comprising a halide salt and an initiator of glass formation;
    a mixing the first and the second reverse microemulsions together such that the components of the micelles of the first precursor reverse microemulsion react with the components of the micelles of the second precursor reverse microemulsion;

to give a nanoparticle comprising one or more silver halide particles embedded in glass, the nanoparticle exhibiting a light-induced, reversible darkening.

2. A method according to claim 1 wherein the soluble silver salt is silver nitrate and the halide salt is sodium chloride.

3. A method according to claim 1 wherein the first precursor reverse microemulsion further comprises a water-soluble copper(I) salt.

4. A method according to claim 1 which comprises the further step of adding a capping agent to the mixture of microemulsions after the nanoparticle has been formed.

5. A method according to claim 4 which comprises the further step of adding a polymer or polymer precursor which reacts with the capping agent.

6. A method according to claim 4 which comprises, following addition of the capping agent, the further steps of:
performing an aqueous extraction; and
collecting the nanoparticle from the aqueous phase.

* * * * *